United States Patent [19]

Ito

[11] Patent Number: 4,988,337
[45] Date of Patent: Jan. 29, 1991

[54] SYRINGE PUMP APPARATUS

[75] Inventor: Yoshio Ito, Fujinomiya, Japan

[73] Assignee: Terumo Kabushiki Kaisha, Tokyo, Japan

[21] Appl. No.: 391,192

[22] Filed: Aug. 8, 1989

[30] Foreign Application Priority Data

Aug. 10, 1988 [JP] Japan .................................. 63-199682

[51] Int. Cl.⁵ .............................................. A61M 5/20
[52] U.S. Cl. ...................... 604/154; 604/67;
604/224; 128/DIG. 12
[58] Field of Search .................. 604/66, 67, 154, 155,
604/208, 224, 245; 128/DIG. 12; 222/390

[56] References Cited

U.S. PATENT DOCUMENTS 4,465,474 8/1984 Mardorf et al. ...................... 604/154
4,544,369 10/1985 Skakoon et al. .
4,767,406 8/1988 Wadham et al. ...................... 604/67

FOREIGN PATENT DOCUMENTS 0229450 7/1987 European Pat. Off. .
0171337 2/1987 France .

WO86/05402 9/1986 PCT Int'l Appl. .

Primary Examiner—Stephen C. Pellegrino
Attorney, Agent, or Firm—Frishauf, Holtz, Goodman & Woodward

[57] ABSTRACT

Disclosed is a syringe pump apparatus adapted to have a syringe mounted thereon so as to supply in a specified amount per specified unit of time an aqueous solution such as medication within the syringe. A first shaft is fixed to a slider for causing a piston portion of the syringe to operate. Between this slider and a drive motor there are provided a block and a second shaft, the block being provided with an overload detecting mechanism. When the movement of the slider is forcedly stopped during a time period in which the slider is being moved through driving of the drive motor, the resulting load is transmitted to the first shaft in response to the forced stoppage of the slider. In accordance with this load, the overload detecting mechanism detects the state of overload of the slider. Then, when the value detected has exceeded a specified value, the drive motor is stopped by a drive halting mechanism.

8 Claims, 4 Drawing Sheets

SYRINGE PUMP APPARATUS

BACKGROUND OF THE INVENTION

The present invention relates to a syringe pump apparatus which is adapted to deliver to and infuse into a patient a specified amount of aqueous solution per specified unit of time from a syringe within which the aqueous solution such as, for example, a medication is accommodated and, more particularly, to a syringe pump apparatus which is equipped with a drive halting mechanism adapted to halt the driving of the pumping operation when an overload has been produced in a slider section.

Conventionally, in this type of syringe pump apparatus, supply of aqueous solution is performed in the following manner. Firstly, a syringe within which an aqueous solution is accommodated is placed on a syringe holding section and, then, a flange portion of this syringe is fitted into an engaging groove formed in the syringe holding section. Then, a piston portion thereof is engaged with an engaging portion formed in a slider section Thus, the syringe is fixed to the syringe pump. Then, after having adjusted the flow rate of the aqueous solution to be infused into a patient, the syringe is pressed from above by a clamp means to thereby fixedly mount the syringe on a main body of the syringe pump apparatus. The height of the syringe is detected by a photosensor provided in the clamp means and the detection signal thus obtained is sent to the slider mechanism. Thus, the distance of the slider to be moved is determined. Thereafter, when a drive motor involved is caused to rotate, the slider mechanism is caused to operate. As a result, a specified amount of aqueous solution is infused from the syringe into the patient by way of a tube.

By the way, in the syringe pump apparatus having the described construction, it is necessary to stop the driving of the syringe pump apparatus when the aqueous solution within the syringe comes to be zero with the result that an outer casing and the slider abut against each other, or when, for example, the tube connected to the syringe has been bent or squeezed with the result that it is impossible to extrude the aqueous solution within the syringe.

A conventional halting mechanism for halting the syringe pump apparatus is arranged as follows. Namely, a drive motor is installed in the casing and has a rotational gear. This rotational gear is caused to mesh with a gear provided on a feed screw for forward movement of the slider via intermediate gears. The feed screw is thereby caused to rotate. On the other hand, the slider section has a pipe shaft on which there is provided a block section, the block section having a shaft provided thereon Said rotation of the feed screw causes the slider to be forwardly moved by the intermeshing of the feed screw with the shaft provided on the block section.

With this construction, when the slider is brought to the stoppage, it results that the rotation of the feed screw is stopped, while the drive motor is rotated. As a result, the gear provided on the feed screw and the intermediate gears cease to be rotated. For this reason, the rotational gear of the drive motor gradually undergoes application of the load. This load is gradually increased to become an overload, by means of the intermediate gears and by way of a spring. This brings about a state wherein a detecting plate connected to the spring is caused to project outside the box concerned. Changes in area of this projected portion of the detecting plate are detected or sensed by a microswith installed outside the drive motor. When the area of that projection has reached a specified value, a stop signal is delivered from the microswitch to the drive motor, thereby stopping the operation of the syringe pump apparatus.

In the conventional syringe pump apparatus having the described construction, the structure or construction of the halting mechanism becomes very complicated and, at the same time, transmitting stages until the pumping operation is stopped are very large in number. Accordingly, there arises a problem that a large amount of time (6 to 8 hours) is required to be spent from the stoppage of the slide to the halt of the pumping operation.

SUMMARY OF THE INVENTION

The present invention has been made in view of the above-described problems inherent in the prior art and an object thereof is to provide a syringe pump apparatus which is simple in structure and which is capable of stopping the pumping operation in a short time when a state of overload has been reached.

In order to solve the above-described problems of the prior art, there is provided a syringe pump apparatus adapted to supply a specified amount of aqueous solution per unit of time from a syringe within which the aqueous solution is accommodated, the syringe pump apparatus comprising a main body of the syringe pump apparatus, syringe holding means provided on the main body for having the syringe placed thereon, a slider for engaging a piston portion of the syringe when the syringe is placed on the main body of the pump apparatus, the slider being slidably mounted on the main body so as to move the piston portion, first shaft means, fixing means for fixing the first shaft means so as to enable the same to move in one with the slider, a drive source for supplying a drive force for sliding movement of the slider, connecting means for disconnectably connecting the drive source and the slider, the connecting means including second shaft means connected to the slider and a block connected to the second shaft means, overload detecting means provided on the block, the overload detecting means being adapted to detect a state of overload of the slider in accordance with the load produced in the first shaft means due to a forced stop of the slider, said load being produced when the sliding movement of the slider is forcedly stopped during a time period in which the slider is being driven by the drive source, and drive halting means capable of operating so as to cause the driving of the drive source to be halted in accordance with a result of the detection made by the overload detecting means.

In addition, in the present invention, the overload detecting means includes an elastic member capable of being deformed in accordance with the load produced in the first shaft means, and a detecting plate capable of being moved in accordance with the deformation of the elastic member, and sensor means for causing the drive halting means to operate at the time when the amount of the detecting plate moved is detected and exceeded a specified value. Furthermore, the invention provides a construction in which the sensor means is constituted by a reflective type photosensor.

In the syringe pump apparatus of the present invention having the above-described construction, the overload detecting means is mounted on the first shaft means adapted to receive the load directly from the slider. For this reason, transmitting stages until the overload is detected are very small in number as compared with the prior art structure, in other words, transmitting path is very short Thus, it becomes possible to detect the state of overload in a very short time. Further, in the syringe pump apparatus of the present invention, when a state of overload is reached and the slider has thus been stopped, this overload is given to the first shaft means. Then, it is transmitted to the elastic member of the overload detecting means provided on the block. As a result, the elastic member is deformed and the detecting plate is moved in accordance therewith. The distance of this movement of the detecting plate is detected by, for example, the reflective type photosensor. When said distance has exceeded a specified value, a stop signal is delivered to the drive source via the drive halting means. Thus, the pumping operation is stopped.

As stated above, according to the present invention, there can be provided a syringe pump apparatus in which the transmitting stages required up to the detection of the overload state acting on the slider are smaller in number than in the prior art, thus enabling detection of the state of overload in a very short time and quick halt of the pumping operation, and which is simple in structure and is capable of reliable operation.

Further, according to a preferred arrangement of the present invention, the first shaft means is constituted by an elongate pipe shaft and the second shaft means of the connecting means is constituted by a shaft passed through that pipe shaft The pipe shaft constituting the first shaft means has one end fixed to a frame of the slider by the fixing means. The fixing means is constituted by a seal nut screwed over said one end of the pipe shaft via a first seal member, the seal nut having a through hole permitting a shaft of the second shaft means to be passed therethrough via a second seal member.

According to a further preferred arrangement of the present invention, the seal nut not only functions to integrally connect the pipe shaft and the slider but also functions to cooperate with the seal members to thereby perform the sealing action. Thus, it is possible to reliably prevent entry into the interior of the pump apparatus via the pipe shaft, of an aqueous solution having attached onto the outside of the main body of the pump apparatus as well as of a cleaning liquid or the like for removal of such aqueous solution Accordingly, it is possible not only to prevent the corrosion of mechanical portions such as those of the motor, but also to eliminate undesirable effects upon distributed-wire portions, due to the liquid having entered the interior of the main body of the pump apparatus. This makes it possible to further improve the reliability of the pumping operation.

Other objects, features and advantages of the present invention will become apparent from the description of an embodiment thereof which will be made with reference to the accompanying drawings.

DESCRIPTION OF THE PREFERRED EMBODIMENT

An embodiment of the present invention will now be described in detail with reference to the drawings.

Figure 1:
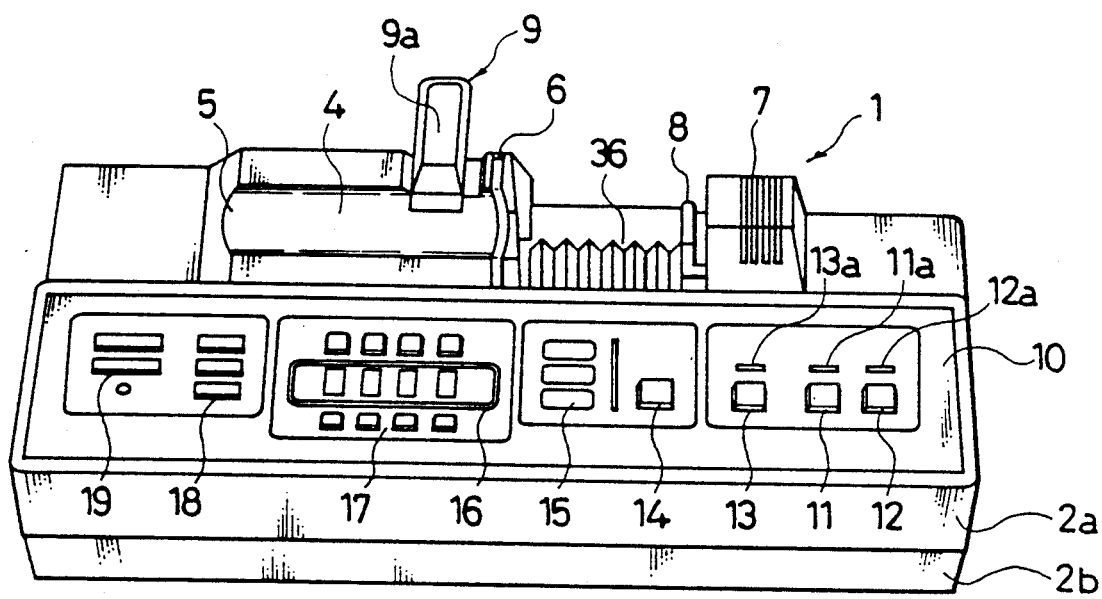
FIG. 1 is a perspective view, taken from the front side, of an outer appearance of a syringe pump apparatus in accordance with an embodiment of the present invention.
Figure 2:
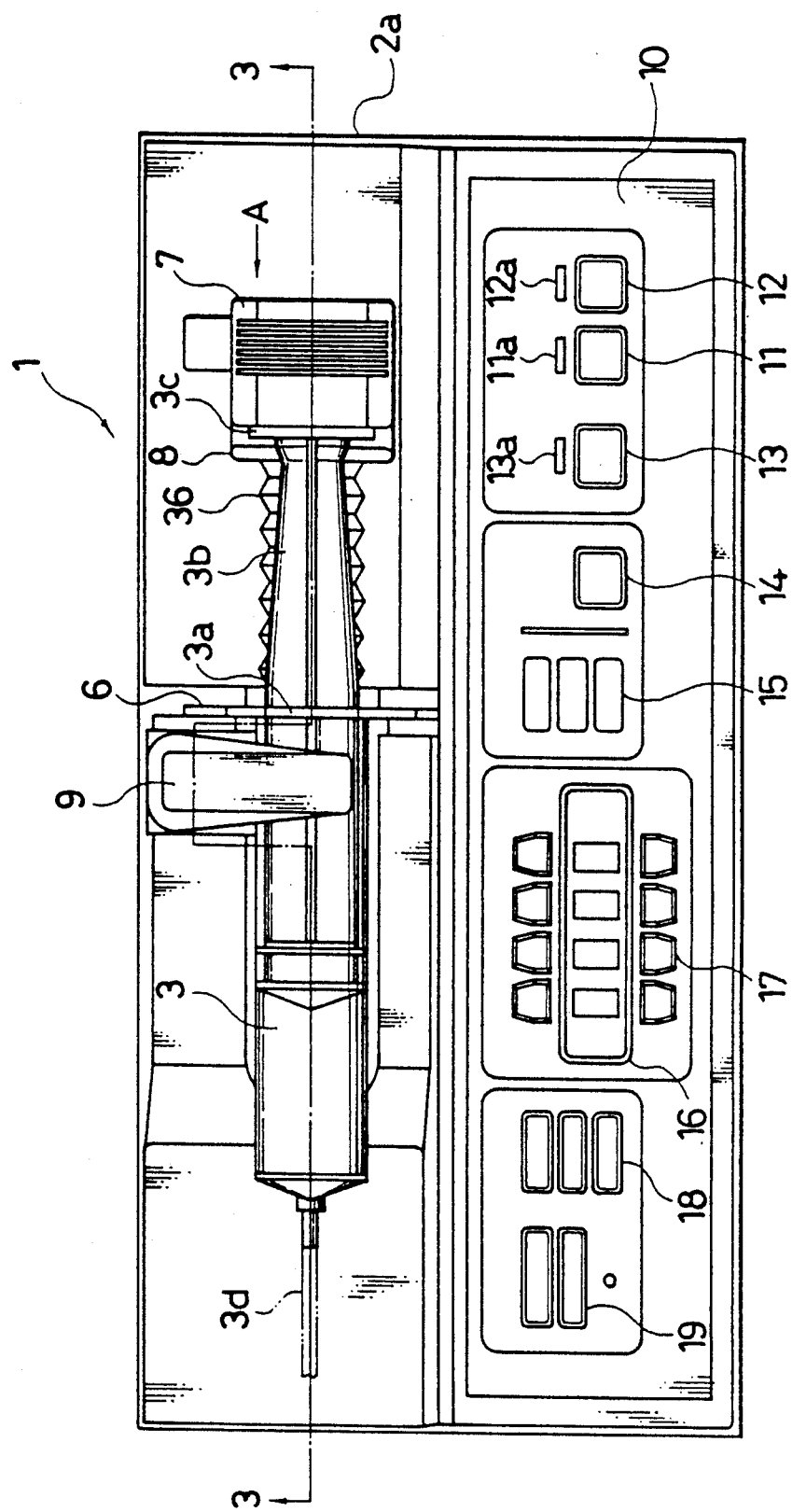
FIG. 2 is a plan view showing a state wherein a syringe is placed on the syringe pump apparatus shown in FIG. 1.

FIG. 1 is a perspective view showing a syringe pump apparatus in accordance with an embodiment of the present invention. FIG. 2 is a plan view showing a state wherein a syringe is installed on the syringe pump apparatus. Referring now to FIGS. 1 and 2, a main body 1 of the syringe pump apparatus has an upper case 2a and a lower case 2b, the upper case 2a being provided, on its top, with a syringe holding section 4 for holding the syringe 3. The syringe holding section 4 is formed with a syringe mounting groove 5 of semicircular shape in cross section so as to permit the syringe 3 to be mounted therein, and an engaging groove 6 for permitting a flange portion 3a of the syringe 3 to be fitted thereinto or engaged therewith. The syringe 3 has a piston portion 3b which has an enlarged end 3c. This enlarged end 3c is adapted to engage an engaging portion 8 of a slider 7 slidably disposed on the main body 1 of the pump apparatus when the syringe 3 has been mounted or placed in the syringe mounting groove 5 as shown in FIG. 2. As the slider moves forward (in the leftward direction indicated by an arrow A in FIG. 2), the piston portion 3b of the syringe 3 is intruded into a main body of the syringe 3. Through the forward movement of the piston portion 3b, an aqueous solution accommodated within the syringe 3 is infused into a patient in a specified amount per specified unit of time from an end portion of the syringe 3 via a tube 3d indicated by a chain line and connected to the syringe 3.

The syringe holding section 4 is provided, at its upper portion, with a clamp means 9 which is shaped like a character L and which has a clamp head 9a, the clamp head 9a being made rockable and made upwardly and downwardly movable. The syringe 3 held on the syringe holding section 4 as in FIG. 2 is pressed from above by the head 9a of the clamp means 9 and thus is fixed by the same. The clamp means 9 is so arranged that the head 9a thereof may have its height adjusted in accordance with, or in conformity with, the size of the syringe 3, that is, the diameter thereof. The height of the clamp head 9a is detected by a magnetic sensor 9b (see FIG. 3) provided in the clamp means 9 and a detection signal thus obtained is delivered as a control signal to the slider 7. In the slider 7, the distance of movement thereof is adjusted or controlled upon receipt of that detection signal. Thus, the stroke of the piston portion 3b of the syringe 3, that is, the amount of the aqueous solution to be delivered per unit of time is determined.

The upper case 2a is further provided with an operation section 10, which includes a start switch 11, start lamp 11a, stop switch 12, stop lamp 12a, fast feed switch 13, fast feed lamp 13a, buzzer stop switch 14, alarm lamp 15, infusion amount display section 16, infusion amount setting switch 17, syringe display lamp 18 and power indication lamp 19.

Figure 3:
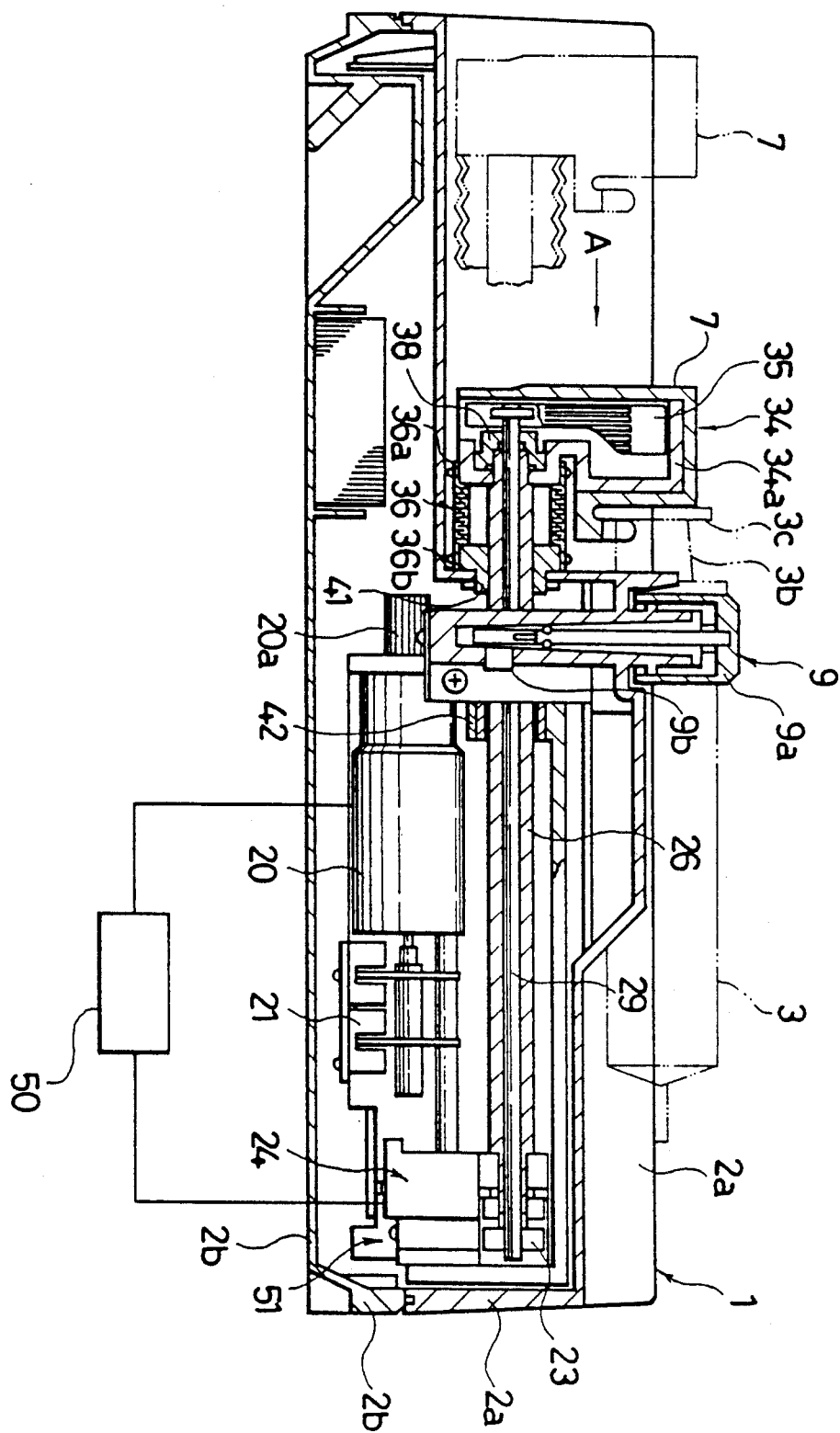
FIG. 3 is a longitudinal sectional view taken along the line 3—3 of FIG. 2.
Figure 4:
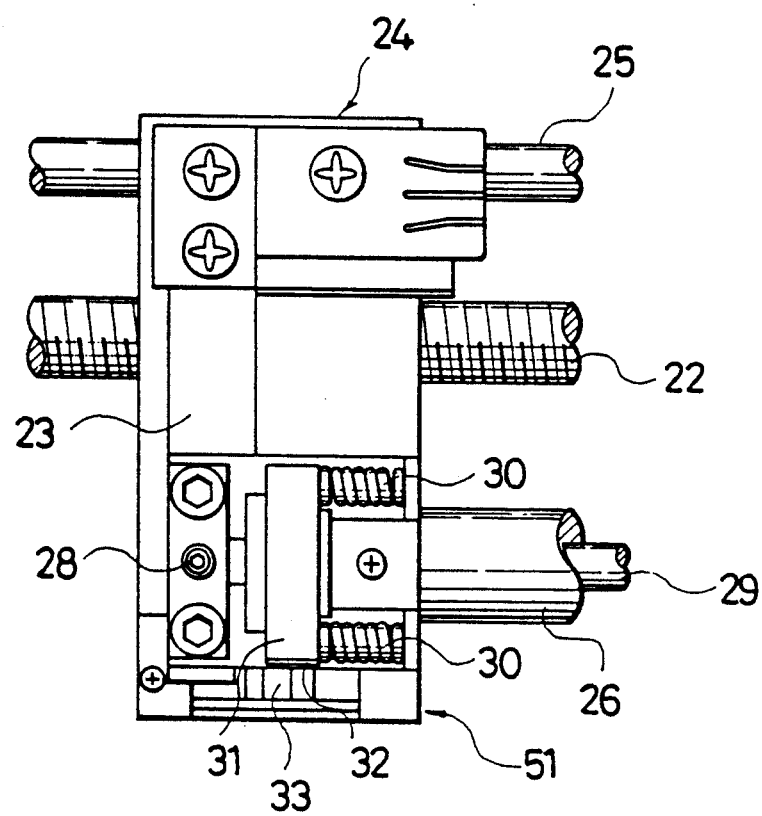
FIG. 4 is an enlarged view, as taken out, of a unit equipped with a drive halting mechanism.
Figure 5:
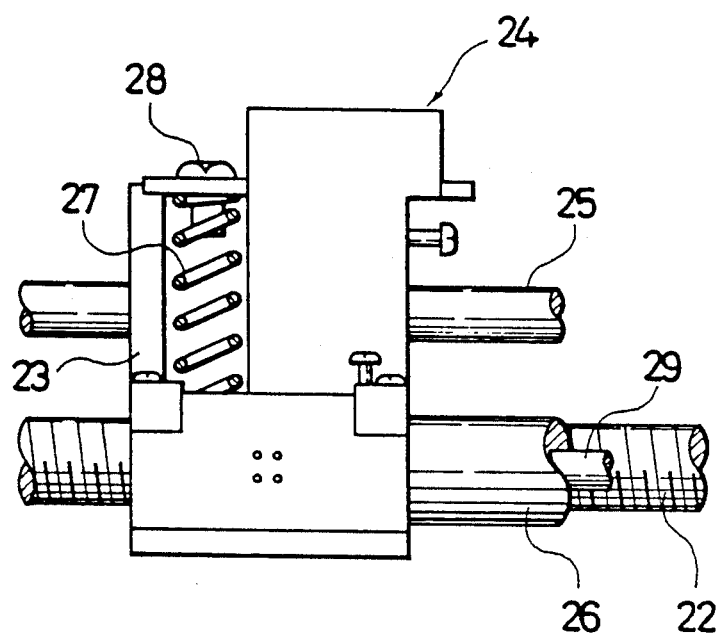
FIG. 5 is a view, as taken from the bottom of the unit shown in FIG. 4.

FIG. 3 is a longitudinal sectional view of the main body 1 of the syringe pump apparatus taken along the line 3—3 of FIG. 2. FIG. 4 is a front view, as taken out, of an overload detecting section in FIG. 3. And, FIG. 5 is a view of the illustration of FIG. 4 as taken from the bottom side thereof A drive motor constituting a drive source is installed within the main body 1 of the pump apparatus Provided in the vicinity of the drive motor 20 is a motor rotation detecting section 21 so as to perform control of the rotational speed of the drive motor 20. The drive motor 20 has an output gear 20a which, although not shown, is connected to a feed screw 22 (FIGS. 4 and 5) via a plurality of gears. Further, this feed screw 22 is connected to a block section 24 via a feed nut 23. The block section 24 is made movable along a guide shaft 25 parallel with the feed screw 22. Further, the slider 7 is so arranged as to make sliding movement in interlocking relation with the movement of the block section 24. The slider 7 and the block section 24 are connected to each other by a pipe shaft serving as a first shaft. That is to say, the drive force of the drive motor 20 is transmitted to the block section 24 via the feed screw 22 and the feed nut 23 and further is transmitted to the slider 7 via the pipe shaft 26. Connected to the feed nut 23 via a clutch spring 27 and a screw 28 is a clutch shaft 29 serving as a second shaft This clutch shaft 29 is connected to a clutch 35 as later described. Through operation of this clutch 35, the feed nut 23 connecting the feed screw 22 and the block section 24 is released, i.e., the connection between the feed screw 22 and the block section 24 is released to render ineffective the transmission of the drive force from the drive motor 20 to the slider 7. It is to be noted that the clutch shaft 29 is passed through the pipe shaft 26. It is to be further noted that the pipe shaft 26 is slidably supported by a bearing 42 provided substantially at the central part of the main body 1 of the pump apparatus.

One end of the pipe shaft 26 at the side of the block section 24 is connected to a detecting plate 31 via an overload spring 30 serving as an elastic member capable of being expanded and constructed in accordance with the magnitude of the load. In consequence, when an overload has been produced in the slider, this overload is transmitted to the overload spring 30 via the pipe shaft 26. In addition, the detecting plate 31 is moved in such a manner that this detecting plate 31 is gradually pulled in accordance with the deformation of the overload spring 30. A reflective mirror 32 is mounted on one side of the detecting plate 31. On the other hand, a reflective type photosensor 33 is mounted on the block section 24 in such a manner as to oppose the reflective mirror 32. This reflective type photosensor 33 is adapted to detect the distance of movement of the detecting plate 31 If said distance of movement reaches or exceeds a specified value, a stop signal is sent to the drive motor 20 via a drive halting mechanism 50 (see FIG. 3) composed of an electric circuit and serving as a drive halting means. The above-mentioned spring 30, detecting plate 31, reflective plate 32 and sensor 33 constitute an overload detecting mechanism 51 serving as an overload detecting means for detecting a state of overload of the slider produced due to stoppage of movement of the slider.

Figure 6:
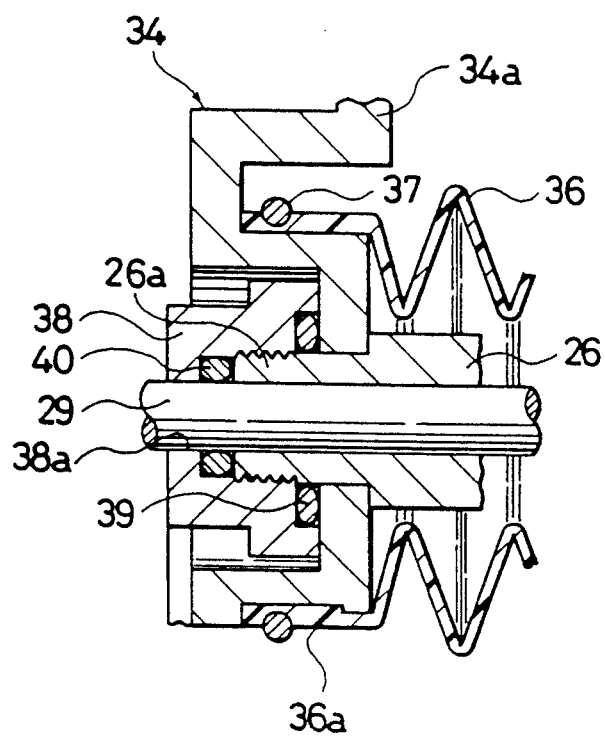
FIG. 6 is a partially enlarged view of a clutch box disposed in a slider.

The slider 7 includes a clutch box 34 and a clutch 35 for operating the slider 7. FIG. 6 is an enlarged view of a sectional construction of the clutch box 34. In the Figure, the clutch box 34 has a frame 34a which is connected to the other end of the pipe shaft 26 for moving the slider 7. The clutch shaft 29 is passed through the pipe shaft 26 and this clutch shaft 29 is connected to the clutch 35. One end 36a of a bellows boot 36 is fixed, by a metal fastener 37, to the frame 34a of the clutch box 34. The other end 36b of the bellows boot 36 is mounted on a joint 41 (see FIG. 3) mounted on the main body of the pump apparatus and the bellows boot covers a portion of the pipe shaft 26 which is allowed to protrude outwardly from the pump apparatus 1.

A reference numeral 38 denotes a seal nut, and it is arranged such that an end portion 26a of the pipe shaft 26 is pressed, by this seal nut 38, against the frame 34a of the clutch box 34 in a state wherein a condition of seal is achieved therebetween. The seal nut 38 constitutes a fixing means for causing the slider 7 to move in one with the pipe shaft 26. An O-ring 39 is interposed at between the seal nut 38 and the frame 34a of the clutch box 34 which are engaged to each other, while an O-ring 40 is interposed between the seal nut 38, the pipe shaft 26 and the clutch shaft 29 which are engaged to each other. Thus, it is possible to prevent unnecessary water and aqueous solution from entering the interior of the main body 1 of the pump apparatus from outside via said end portion of the pipe shaft 26. It is to be noted that the shaft 29 is inserted through a through bore 38a of the seal nut 38.

The operation of the above-constructed syringe pump apparatus having the described construction will now be described. First of all, the head 9a of the clamp 9 is rocked in the lateral direction. In this state, the syringe 3 within which an aqueous solution is accommodated is mounted in the syringe mounting groove 5 of the syringe holding section 4. The flange portion 3a of the syringe 3 is fitted into the engaging groove 6 and, at the same time, the enlarged end 3c of the piston portion 3b of the syringe 3 is engaged with a U-shaped engaging portion 8 provided in the slider 7. Thus, the syringe 3 is fixedly mounted on the syringe pump apparatus. Next, after having adjusted the flow rate of the aqueous solution to be infused into a patient, the head 9a of the clamp means 9 is returned back to the original position. Then, the syringe 3 is pressed from above by the clamp head 9a and is thereby fixed. The height of the clamp section 9 is detected by a magnetic sensor 9b for detecting the height level of the clamp means 9. The detection signal thus obtained is delivered to the slider 7. As a result, the distance of movement of the slider 7, i.e., the amount of the aqueous solution to be supplied per unit of time is determined.

Thereafter, when the drive motor 20 is driven to rotate, the drive force is transmitted to the slider 7 via the feed screw 22, feed nut 23, block section 24 and pipe shaft 26. By the forward movement of the slider 7 indicated by the arrow A in FIGS. 2 and 3, the piston portion 3b of the syringe 3 is forwardly moved into the syringe 3. Thus, a specified amount of the aqueous solution is infused per specified unit of time into a patient from the syringe 3 by way of the tube 3d.

In the above-mentioned series of operational process steps, the drive halting mechanism is caused to operate in the following cases. Namely, where, for example, the aqueous solution within the syringe 3 becomes zero with the result that the slider abuts against the upper casing of the pump apparatus to have its motion forcedly stopped, or where the tube 3d connected to the syringe pump or any portion of a liquid supply piping has its liquid passage forcedly stopped for some reason such as, for example, bending or squeezing of the tube, piping, and the like to thereby disable the extrusion of the aqueous solution within the syringe, the drive halting mechanism is caused to operate. That is to say, in such cases, since the drive motor 20 is still driven to rotate, the feed screw 22 continues to be rotated. Therefore, the clutch shaft 29 connected to the feed screw 22 via the feed nut 23, also, becomes likely to move.

Since, however, the slider is kept in a state of forced stoppage, the resulting load is transmitted to the pipe shaft which remains similarly unmoved. Further, the load is transmitted to the overload detecting mechanism 51 connected to this pipe shaft 26. When the overload is transmitted to the overload spring 30, the detecting plate 31 is gradually moved in such a manner as to be pulled in accordance with the deformation of the overload spring 30 which has thus been overloaded. Thus, the distance of movement of the detecting plate 31 is detected by the reflective type photosensor 33. When said distance of movement of the detecting plate 31 has reached, or has exceeded, a specified value, a stop signal is sent from the reflective type photosensor 33 to the drive motor 20 via the drive halting mechanism 50. Thus, the rotation of the drive motor 20 is stopped.

As has been stated before, the drive halting mechanism of the well-known syringe pump apparatus is arranged such that a state of overload is detected by way of a multistage transmission mechanism. For this reason, a very large amount of time was required until the pumping operation is halted In the syringe pump apparatus according to this embodiment, since the overload detecting mechanism is mounted on the pipe shaft which undergoes direct application of the overload, the stages via which the state of overload is detected are very small in number. More specifically, according to this embodiment, it is possible to detect a state of overload in a very short time of about 15 to 20 minutes and thereby halt the driving of the motor.

Although the present invention has been described by way of the embodiment thereof, the invention is not limited to the above-described embodiment but various modifications and changes thereof may be made without departing from the subject matter thereof.

What is claimed is:

1. A syringe pump apparatus adapted to supply a specified amount of aqueous solution per unit of time from a syringe within which the aqueous solution is accommodated, comprising:
a main body of the syringe pump apparatus;
syringe holding means provided on said main body for having said syringe placed thereon;
a slider for engaging a piston portion of said syringe when said syringe is placed on said main body of the pump apparatus, said slider being slidably mounted on said main body so as to move said piston portion;
first shaft means;
fixing means for fixing said first shaft means for enabling said first shaft means to move as one with said slider;
a drive source for supplying a drive force for causing sliding movement of said slider;
connecting means for disconnectably connecting said drive source and said slider, said connecting means including second shaft means coupled to said slider and a block coupled to said second shaft means;
overload detecting means provided on said block, said overload detecting means being coupled to said first shaft means and including means for detecting a state of overload of said slider in accordance with a load produced in said first shaft means due to a forced stop of said slider, said load being produced when sliding movement of said slider is forcedly stopped during a time period in which said slider is being driven by said drive source; and
drive halting means including means coupled to said drive source and being responsive to said overload detecting means for causing the driving of said drive source to be halted in accordance with a result of the detection made by said overload detecting means.

2. The syringe pump apparatus as set forth in claim 1, wherein said overload detecting means includes:
an elastic member capable of being deformed in accordance with the load produced in said first shaft means,
a detecting plate which is movable in accordance with the deformation of said elastic member, and
sensor means for causing said drive halting means to operate at a time when the amount that said detecting plate has moved is detected to exceed a specified value, whereby the driving of said drive source is halted.

3. The syringe pump apparatus as set forth in claim 2, wherein said sensor means comprises a reflective type photosensor.

4. The syringe pump apparatus as set forth in claim 1, wherein:
said first shaft means comprises an elongate pipe shaft, and
said second shaft means of said connecting means comprises a shaft passed through said pipe shaft.

5. The syringe pump apparatus as set forth in claim 4, wherein;
said pipe shaft of said first shaft means has one end fixed to a frame of said slider by said fixing means,
said fixing means comprises a seal nut screwed over said one end of said pipe shaft via a first seal member, and
said seal nut having a through hole permitting a shaft of said second shaft means to be passed therethrough via a second seal member.

6. The syringe pump apparatus as set forth in claim 1, wherein said drive halting means is electrically coupled to said drive source.

7. The syringe pump apparatus as set forth in claim 6, wherein said drive halting means includes means for sending a stop signal to said drive source responsive to said detection made by said overload detecting means.

8. The syringe pump apparatus as set forth in claim 1, wherein said drive halting means includes means for sending a stop signal to said drive source responsive to said detection made by said overload detecting means.

* * * * *